United States Patent [19]
Dallmier et al.

[11] Patent Number: 5,866,511
[45] Date of Patent: Feb. 2, 1999

[54] STABILIZED SOLUTIONS OF BROMONITROMETHANE AND THEIR USE AS BIOCIDES

[75] Inventors: Anthony W. Dallmier, Naperville, Ill.; Enrico J. Termine, Baton Rouge, La.; Alan M. Yeoman, Duluth, Ga.

[73] Assignee: Great Lakes Chemical Corporation, West Lafayette, Ind.

[21] Appl. No.: 856,874

[22] Filed: May 15, 1997

[51] Int. Cl.$^6$ ..................................................... A01N 33/18
[52] U.S. Cl. ............................................ 504/150; 514/740
[58] Field of Search .............................. 514/740; 504/150

[56] References Cited

U.S. PATENT DOCUMENTS

| | | | |
|---|---|---|---|
| 2,987,479 | 6/1961 | Bennett | 252/51.5 |
| 5,180,859 | 1/1993 | Timberlake et al. | 568/946 |

OTHER PUBLICATIONS

Clark, Nigel G.; Croshaw, Betty; Leggetter, Brian E. and Spooner, David F., "Synthesis and Antimicrobial Activity of Aliphatic Nitro Compounds", *Journal of Medicinal Chemistry,* 1974, vol. 17, No. 9, pp. 977–981.

"Antimicrobial Activity of a Series of Hato–Nitro Compounds," W.R. Bowman and R.J. Stretton, *Antimicrobial Agents and Chemotherapy,* Dec. 1972, vol. 2, No. 6, pp. 504–505.

"Synthesis and Study of the Physiological Activity of Aliphatic Nitro Compounds," Fridman, Zalesov, Surkov, Kratynskaya and Plaksina, *Pharm. Chem. Journ.,* vol. 10, 1976, pp. 752–755.

"The Reaction of Geminal Bromonitroalkanes with Nucleophiles. Part 1. The Decomposition of 2–Bromo–2–nitropropane–1,3–diol ('Bronopol') in Aqueous Base," Brian C. Challis and Taher I. Yousaf, *J. Chem. Soc. Perkin Trans. 2,* 1991, pp. 283–286.

"Structure and Antimicrobial Properties of Certain Bromonitro Compounds," Bartoshevich, Kopranenkov, Burdelev and Unkovskii, *Pharm. Chem. J.,* Vo. 6(1), 1972, pp. 11–13.

*Primary Examiner*—Allen J. Robinson
*Attorney, Agent, or Firm*—Woodard, Emhardt, Naughton Moriarty & McNett

[57] ABSTRACT

Stable solutions of bromonitromethane are prepared and shown to be useful as an antimicrobial in a broad spectrum of applications. Bromonitromethane is applied using a stable aqueous solution or is generated from products which act as bromonitromethane donors. Bromonitromethane solutions are stabilized by the addition of a mineral acid.

28 Claims, 1 Drawing Sheet

STABILIZED SOLUTIONS OF BROMONITROMETHANE AND THEIR USE AS BIOCIDES

FIELD OF THE INVENTION

The present invention relates generally to biocides, and more particularly to stabilized solutions of bromonitromethane which are antimicrobially effective against bacteria, algae and fungi.

BACKGROUND OF THE INVENTION

Nonoxidizing antimicrobials are useful in many industrial systems including water systems, pulp and paper manufacturing, metal working fluid preservation, latex paint preservation, wood preservation, cosmetics preservation, and oil field and institutional hard-surface disinfection. However, despite the many commercially available nonoxidizing antimicrobials, none are entirely suitable for every application due to issues relating to efficacy, safety, environmental acceptability and cost.

Compounds containing gem bromonitro functionality have been shown to possess antimicrobial activity. The simplest of those compounds, bromonitromethane is reported to possess antimicrobial activity, but is also known to be unstable and unsuitable for commercial use. For example, Clark et al., in "Synthesis and Antimicrobial Activity of Aliphatic Nitro Compounds" state: "Bromonitromethane . . . inhibited all the organisms . . . but gave inconsistent results. This was attributed to the volatility of the compound, and it was not tested further." See, Clark et al., 17 *J. Med. Chem.* 977–81 (1974).

It can be seen from the above that the prior art has failed to develop practical application technology for the use of bromonitromethane as an effective industrial nonoxidizing biocide. A need therefore exists for stable solutions of bromonitromethane that can be used as antimicrobial agents against a broad spectrum of bacteria, algae and fungi. The present invention addresses that need.

SUMMARY OF THE INVENTION

The present invention provides stable, biocidally effective solutions of bromonitromethane by providing the bromonitromethane in a solution stabilized by the addition of mineral acid. The stable, acidified solutions of bromonitromethane are effective as a broad spectrum industrial antimicrobial agent, and can be used in water treatment, paint, pulp and paper manufacturing, metal working fluids, and other non-oxidizing biocide applications. Acidified solutions of bromonitromethane are effective against a wide spectrum of bacteria, algae, and fungi.

DESCRIPTION OF THE PREFERRED EMBODIMENT

Figure 1:
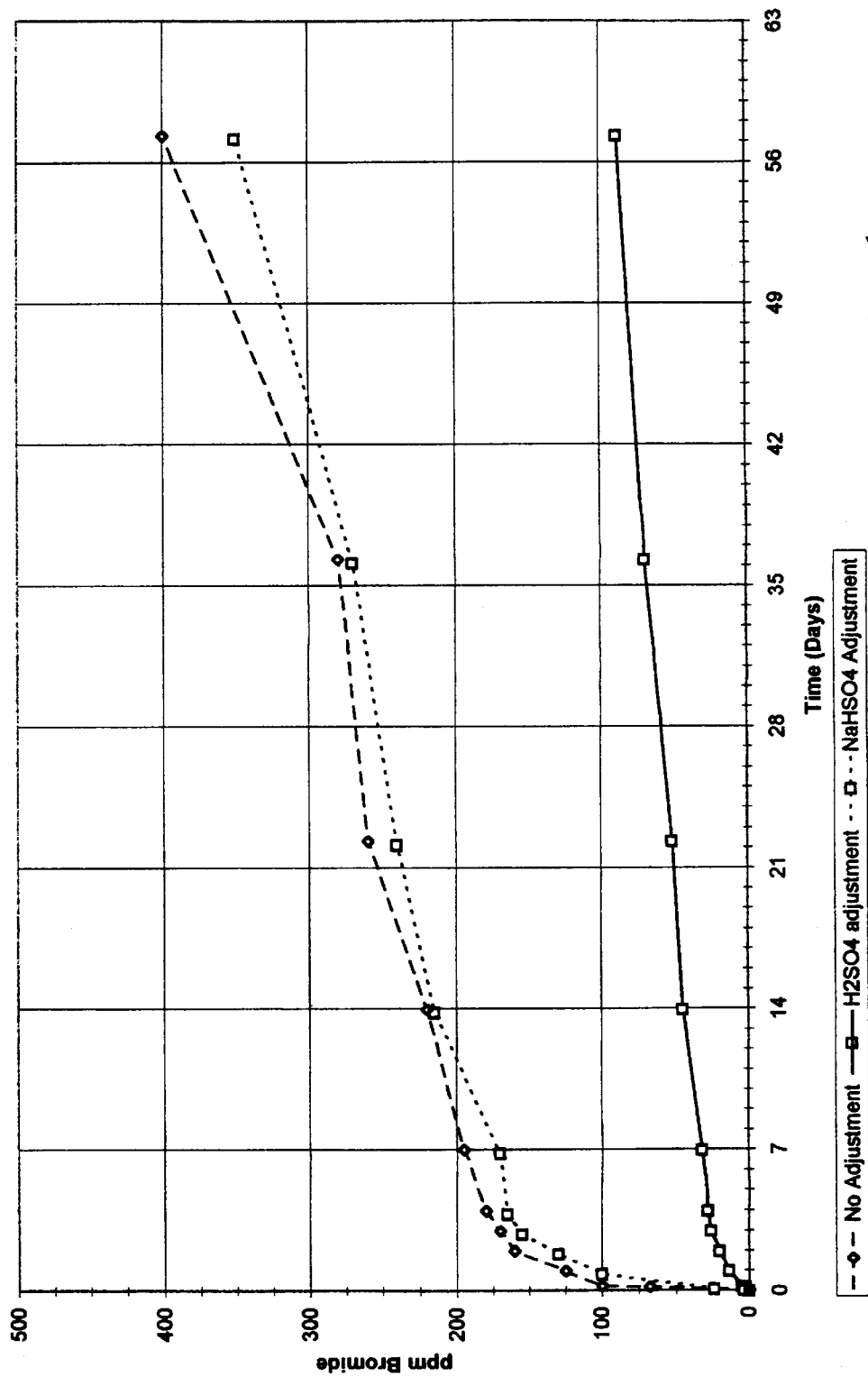
FIG. 1 is a graph of bromide ion generation in BNM formulations.

For the purpose of promoting an understanding of the principles of the invention, reference will now be made to preferred embodiments and specific language will be used to describe the same. It will nevertheless be understood that no limitation of the scope of the invention is thereby intended, such alterations and further modifications in the preferred embodiments, and such further applications of the principles of the invention as described herein being contemplated as would normally occur to one skilled in the art to which the invention pertains.

The present invention relates generally to compositions and methods for protecting aqueous media from microbial attack. In one preferred embodiment, a stable, acidified solution of bromonitromethane is used to inhibit microbial growth. Particularly preferred embodiments of the invention inhibit microbial growth in paint, cooling water, paper pulp, borate solutions, etc.

The solutions of bromonitromethane are stabilized by the addition of mineral acid. The solutions are preferably acidified with acids such as HCl, $H_2SO_4$ and $HNO_3$. Other acids may of course be used, as will be appreciated by persons skilled to the art.

The biocides of the present invention are effective against a wide range of microbes, including bacteria, algae and fungi. For example, the acidified BNM solutions of the present invention have been shown to be effective for inhibiting the growth of *Pseudomonas aeruginosa* and *Aspergillus niger*, sulfate reducing bacterium such as *Desulfovibrio desulfuricans*, and algal genera such as Anabeana, Chlamydomonas and Chlorella.

One preferred embodiment of the present invention provides solutions which may be introduced into a water treatment system for use as an antimicrobial. The inconsistent results obtained by the prior art are not obtained with the stabilized bromonitromethane solutions. Problems with solubility associated with a number of other commercial nonoxidizing biocides are also eliminated.

Some commercial nonoxidizing biocides act by donating bromonitromethane. If the degradation of these parent compounds is controlled, then the long term release of the biocidal moiety bromonitromethane into solution may be achieved. Some commercial nonoxidizing biocides which may release bromonitromethane are: 2-(2-bromo-2-nitroethenyl) furan, 2-bromo-2-nitropropane-1,3-diol, and (β-bromo-β-nitro)styrene.

Reference will now be made to specific examples using the processes described above. It is to be understood that the examples are provided to more completely describe preferred embodiments, and that no limitation to the scope of the invention is intended thereby.

EXAMPLE 1

Determination of enhanced formulation stability for solutions of bromonitromethane.

A study was performed to determine if aqueous concentrates of BNM could be prepared with adequate storage stability to make the material useful as a biocide. Results indicate BNM can be stabilized by acidifying the BNM with a strong mineral acid. The most stable solution (acidified with $H_2SO_4$ to a pH 2.3) had a degradation rate of only 0.4% BNM per 50 days. Less acidified solutions had faster degradation rates.

BNM (4.58 g, 91.4% assay) was dissolved in 100 mL of deionized water sample 1. A pH 2.37 solution was prepared by adding one drop of sulfuric acid to 100 mL DI water and then adding 4.60 g of the BNM sample 2. A pH 3.76 solution was prepared by adding one drop of 10% aq sodium hydrogen sulfate to 100 mL DI water and then adding 4.60 g of the BNM sample 3. A pH 7.91 solution was prepared by dissolving 4.60 g of the BNM in 100 mL of DI water. A total of 7.2 g of 16.4% NaOH was then added over six minutes to maintain the pH. That solution turned red, indicating the presence of the bromonitromethylate anion and was slowly becoming acidic before the initial bromide value was determined. Gas chromatography of this sample showed that over 99% of the BNM had decomposed. As that sample was stored, off-gassing ($CO_2$) was observed.

Each solution was measured for bromide ion concentration using ion selective electrodes over the course of 57 days to determine the degree of hydrolysis.

The rate of bromide formation was faster for the non-acidified solutions. The bromide ion formation vs. time was plotted as shown in FIG. 1.

Stability testing over a broad range of initial pH values, using bromide ion concentration as an indicator of BNM decomposition over a 57 day period demonstrated that addition of mineral acid stabilized BNM formulations. Unadjusted solutions (sample 1) and $NaHSO_4$ adjusted solutions (sample 3) continued to decomposed as higher rates than the $H_2SO_4$ adjusted formulation (sample 2) even after the pH dropped below 4. In fact, the cumulative degradation of samples 1 and 3 are nearly the same, which suggests that biosulfate was ineffective as a stabilizer. See FIG. 1.

Aqueous solutions of BNM are stabilized by the addition of acid. The material hydrolyzes at a very slow rate, giving a half life of over 10 years. Non-acidified BNM solutions hydrolyze rapidly and, in fact, this is a means of disposal for the material.

EXAMPLE 2

Procedure for preparing stable, acidified bromonitromethane solutions.

An acidified solution of bromonitromethane (BNM) is prepared by adding one drop of sulfuric acid to 100 ml distilled water and then adding 4.60 g of BNM (91.4% assay). The solution is sampled for gas chromatography assay at the beginning and end of these studies to confirm the BNM concentration. Aqueous solutions of BNM were stable when acidified with mineral acids to acidic pHs. The material hydrolyzed at a very slow rate giving a half-life of over ten years.

In a similar manner, acidified bromonitromethane solutions having pHs of about 1.0, 1.5, 2.0, 2.5, 3.0, 3.5 and 4.0 are prepared. Testing determined that BNM solutions acidified with strong acids to a pH of between about 2.0 and about 3.0 are the most stable, with the optimum pH being about 2.3.

EXAMPLE 3

Method of inhibiting microbial growth in paint.

Water based paints are subject to microbial attack which could produce viscosity loss or offensive odors. Biocides are added to protect the paint from such degradation in the can. A paint sample was artificially contaminated with *Pseudomonas aeruginosa,* a bacterium which is frequently found in spoiled paint. One milliliter of this paint was used to contaminate a 50 g sample of heat treated paint which had previously been shown to be bacteria-free. The thermal treatment inactivates residual biocide present in the paint.

Acidified solutions of BNM (pH ranging from 1.5 to 3.5) are diluted with sterile water and added at various concentrations to the paint. Positive controls are established by the omission of BNM addition.

A sterile swab was dipped into the paint and samples are plated onto tryptone glucose extract agar (TGEA; Difco, Detroit, Mich.). Samples of contaminated paint are subsequently swabbed onto sterile TGEA after 1,2,3,7, and 14 days of incubation of 25° C. The plates are incubated for one week at 25° C. Any growth observed on the agar surface during the incubation period is noted. All positive controls exhibit bacterial growth. The minimum inhibitory concentration (MIC), defined as the lowest concentration of BNM which prevented bacterial growth in the paint, is determined for the inventive solutions. Representative results are shown below.

| Action of Bromonitromethane Against Pseudomonas Aeruginosa in Paint | |
|---|---|
| Incubation Period (Days) | Minimum Inhibitory Concentration (ppm) |
| 1 | 2–5 |
| 2 | 2–5 |
| 3 | 2–5 |
| 7 | 2–5 |
| 14 | 2–5 |

EXAMPLE 4

Method of inhibiting the growth of sulfate reducing bacterium (SRB) in aqueous media.

API broth (Difco, Detroit, Mich.) is inoculated with the sulfate reducing bacterium (SRB) *Desulfovibrio desulfuricans* ($10^4$ cells/ml). Stable, acidified solutions of bromonitromethane (pH ranging from 1.5 to 3.6) are added to provide bromonitromethane at various concentrations to the SRB cultures. A positive control is constructed in the same fashion with BNM addition.

The cultures are housed in a GasPak® jar (Becton Dickinson Microbiology Systems, Cockeysville, Md.) under anaerobic conditions (4–10% $CO_2$, <1% $O_2$) at ambient temperature. Cultures are checked weekly for a period of three weeks for visible block growth indicative of SRB's. All positive controls exhibit growth. The minimum inhibitory concentration (MIC), defined as the lowest concentration of BNM which prevented bacterial growth in the API broth tubes, is determined. Representative results are shown below.

| Bromonitromethane Activity Against the Sulfate Reducing Bacterium Desulfovibrio Desulfuricans (pH = 2.37) | |
|---|---|
| Incubation Period (weeks) | Minimum Inhibitory Concentration (ppm) |
| 1 | <0.1 |
| 2 | 0.1–0.5 |
| 3 | 0.1–0.5 |

EXAMPLE 5

Method of inhibiting the growth of fungi in aqueous media.

Industrial water presents a favorable environment for fungal growth. Fungi can cause many problems in industrial systems including damage to cooling tower wood fill and decks by delignification. Synthetic water is prepared according to the following formula: 0.2 mM $MgSO_4$, 1.2 mM $CaCl_2$ and 1.0 mM $NaHCO_3$. Cooling water presents a favorable environment for microbiological growth. Fungi can damage the cooling tower wood fill and decks by delignification. Synthetic cooling water (CW) is prepared according to the following formula: 0.2 mM $MgSO_4$, 1.2 mM $CaCl_2$, and 1.0 mM NaHCO. The pH is adjusted to either 6 or 8 with either $H_2SO_4$ or NaOH. The resulting solution is then sterilized by passing through a 0.2 μm filter. Various concentrations of acidified BNM solution (pH ranging from 1.5 to 4.0) are added to aliquots of sterile synthetic water. A positive control is prepared by omitting the BNM.

Three day old cultures of *Aspergillus niger* (ATCC 9642) are harvested from the surface of potato dextrose agar (Difco, Detroit, Mich.) supplemented with tartaric acid. The samples are dosed with *A. niger* to achieve a concentration of $10^3$ CFU/ml. These samples are incubated for one week at ambient temperature. The cultures are plated onto PDA in order to recover any surviving mold. These plates are incubated for three days at ambient temperature. All positive controls exhibit growth. The minimum inhibitory concentration (MIC), defined as the lowest concentration of BNM which prevented fungal growth on the PDA plates, is determined. Representative results are given in the following Table.

| ANTIFUNGAL ACTION OF BROMONITROMETHANE AGAINST ASPERGILLUS NIGER | |
|---|---|
| pH | Minimum Inhibitory Concentration (ppm) |
| 6 | <1 |
| 8 | 1–5 |

EXAMPLE 6

Method of inhibiting algal growth in aqueous media.

Pure cultures of the algal genera Anabeana, Chlamydomonas, and Chlorella are used to inoculate Allens medium at pH 7.5 achieving a final concentration of $10^4$ cells/ml. All tests are performed on pure cultures. Various concentrations of acidified BNM solution (for each pH across the pH range of 1.5 to 3.5) are added to the culture tubes. Positive controls are established by the omission of BNM.

The algal cultures are housed in a light box (400 ft. candles; light source—cool white fluorescent tubes; 16 h on/8 h off cycles; 22°–26° C.) for three weeks. The cultures are read weekly noting any turbidity and green coloration of the medium which would indicate a positive result. All positive controls exhibit luxurious algal growth during the course of incubation. The minimum inhibitory concentration was determined, with representative results being shown below.

| ANTIALGAL ACTIVITY OF BROMONITROMETHANE | |
|---|---|
| Genus | Minimum Inhibitory Concentration (ppm) |
| Anabeana | 0.5–1.0 |
| Chlamydomonas | 0.1–0.5 |
| Chlorella | 0.5–1.0 |

EXAMPLE 7

Method of inhibiting the growth of aerobic bacteria in aqueous media.

Borate buffer (25 mM) is adjusted to either pH 7 or 8. The buffer was sterilized by passing through a 0.2 μm filter. *Pseudomonas aeruginosa* (ATCC 278853) is added to aliquots of the sterile buffer to achieve a final concentration of $10^6$ cells/ml. This population is confirmed by serially diluting a sample in sterile phosphate buffer (0.3 mM) and plating onto tryptone glucose extract agar (TGEA; Difco, Detroit, Mich.). Acidified solutions of bromonitromethane are added at various concentrations to the test cultures. Solutions acidified with acids to pHs of between 1.5 and 3.5 are prepared and tested. Positive controls are established by omitting BNM from the test samples.

Following 3 and 24 hour exposure periods at ambient temperature, the resulting test suspensions are diluted and plated as previously described. All plates are enumerated following an incubation period of 24 hr. at 37° C. The minimum inhibitory concentration is defined as the lowest concentration which decreased the microbial population by at least 90% over the period tested. Results are presented in the following Table.

| BROMONITROMETHANE ACTION IN BORATE BUFFER vs. PSEUDOMONAS AERUGINOSA | | |
|---|---|---|
| | Minimum Inhibitory Concentration (ppm) | |
| Incubation | pH7 | pH8 |
| 3 | 0.6–3.2 | 0.6–3.2 |
| 24 | 0.3–0.6 | 0.3–0.6 |

EXAMPLE 8

Method of inhibiting microbial growth in alkaline mixtures of paper pulp.

Microbial growth at various points in a paper making system could produce a slime layer which could drop onto the paper sheet causing product damage and machine downtime due to breaks. Biocides are added to keep the microbial growth in check throughout the system. A pulp slurry (1.25% dry basis) was prepared in sodium phosphate buffer (200 mM, pH 8). The slurry is sterilized by autoclaving at 121° C. for 20 min. *Pseudomonas aeruginosa* (ATCC 27853) is added to the sterile pulp slurries to achieve a final concentration of $10^6$ cells/ml. This population is confirmed by serially diluting a sample in sterile phosphate buffer (0.3 mM) and plating onto tryptone glucose extract agar (TGEA; Difco, Detroit, Mich.). Bromonitromethane is added at various concentrations to the test cultures. Controls are established by omitting BNM from the test samples. Following a 3 and 24 hr. exposure period at ambient temperature, the resulting test suspensions are diluted and plated as previously described. All plates are enumerated following an incubation period of 24 hr. at 37° C. The minimum inhibitory concentration is defined as the lowest concentration which decreased the microbial population by at least 90% over the period tested. Typical results are presented below.

| BROMONITROMETHANE ACTION IN ALKALINE PULP (pH8) vs. PSEUDOMONAS AERUGINOSA | |
|---|---|
| Incubation Period | Minimum Inhibitory Concentration (ppm) |
| 3 | 1–5 |
| 24 | <1 |

EXAMPLE 9

Inhibition of $CO_2$ Off-Gassing.

The solutions of the present invention provide the additional benefit of minimizing off-gassing of $CO_2$ during storage of the solution. That benefit is demonstrated by storing unstabilized BNM and stabilized BNM under standard conditions. The stabilized BNM solutions substantially reduce off-gassing ($CO_2$) when compared to non-stabilized solutions.

While the invention has been illustrated and described in detail in the drawing and foregoing description, the same is to be considered as illustrative and not restrictive in character, it being understood that only the preferred embodiment has been shown and described and that all changes and modifications that come within the spirit of the invention are desired to be protected.

What is claimed is:

1. A method of inhibiting microbial growth in aqueous media, comprising adding to a microbe-containing aqueous media an acidified solution of bromonitromethane in an amount sufficient to inhibit the growth of microbes in the media.

2. A method according to claim 1 wherein said adding step comprises adding to the aqueous media a solution of bromonitromethane acidified with a mineral acid to a pH of less than about 4.0.

3. A method according to claim 2 wherein said adding step comprises adding to the aqueous media a solution of bromonitromethane acidified with a mineral acid to a pH of between about 1.5 and about 3.5.

4. A method according to claim 3 wherein said adding step comprises adding to the aqueous media a solution of bromonitromethane acidified with a mineral acid to a pH of between about 2.0 and about 3.0.

5. A method of inhibiting microbial growth in a water-based paint, comprising adding to the aqueous paint an acidified solution of bromonitromethane in an amount sufficient to inhibit the growth of microbes in the paint.

6. A method according to claim 5 wherein said adding step comprises adding to the aqueous paint a solution of bromonitromethane which is acidified with a mineral acid to a pH of less than about 4.0.

7. A method according to claim 6 wherein said adding step comprises adding to the aqueous paint a solution of bromonitromethane which is acidified with a mineral acid to a pH of between about 1.5 and about 3.5.

8. A method according to claim 7 wherein said adding step comprises adding to the aqueous paint a solution of bromonitromethane which is acidified with a mineral acid to a pH of between about 2.0 and about 3.0.

9. A method of inhibiting the growth of sulfate reducing bacteria in an aqueous media, comprising adding to a sulfate reducing bacteria-containing aqueous media an acidified solution of bromonitromethane in an amount sufficient to inhibit the growth of microbes in the media.

10. A method according to claim 9 wherein said adding step comprises adding to the aqueous media a solution of bromonitromethane which is acidified with a mineral acid to a pH of less than about 4.0.

11. A method according to claim 10 wherein said adding step comprises adding to the aqueous media a solution of bromonitromethane which is acidified with a mineral acid to a pH of between about 1.5 and about 3.5.

12. A method according to claim 11 wherein said adding step comprises adding to the aqueous media a solution of bromonitromethane which is acidified with a mineral acid to a pH of between about 2.0 and about 3.0.

13. A method of inhibiting microbial growth in cooling water, comprising adding to the cooling water an acidified solution of bromonitromethane in an amount sufficient to inhibit the growth of microbes in the water.

14. A method according to claim 13 wherein said adding step comprises adding to the cooling water a solution of bromonitromethane which is acidified with a mineral acid to a pH of less than about 4.0.

15. A method according to claim 14 wherein said adding step comprises adding to the cooling water a solution of bromonitromethane which is acidified with a mineral acid to a pH of between about 1.5 and about 3.5.

16. A method according to claim 15 wherein said adding step comprises adding to the cooling water a solution of bromonitromethane which is acidified with a mineral acid to a pH of between about 2.0 and about 3.0.

17. A method of inhibiting algal growth in an aqueous media, comprising adding to an algae-containing aqueous media an acidified solution of bromonitromethane in an amount sufficient to inhibit the growth of algae in the media.

18. A method according to claim 17 wherein said adding step comprises adding to the aqueous media a solution of bromonitromethane which is acidified with a mineral acid to a pH of less than about 4.0.

19. A method according to claim 18 wherein said adding step comprises adding to the aqueous media a solution of bromonitromethane which is acidified with a mineral acid to a pH of between about 1.5 and about 3.5.

20. A method according to claim 19 wherein said adding step comprises adding to the aqueous media a solution of bromonitromethane which is acidified with a mineral acid to a pH of between about 2.0 and about 3.0.

21. A method of inhibiting microbial growth in a borate buffer solution, comprising adding to the borate buffer solution an acidified solution of bromonitromethane in an amount sufficient to inhibit the growth of microbes in the buffer solution.

22. A method according to claim 21 wherein said adding step comprises adding to the borate buffer solution a solution of bromonitromethane which is acidified with a mineral acid to a pH of less than about 4.0.

23. A method according to claim 22 wherein said adding step comprises adding to the borate buffer solution a solution of bromonitromethane which is acidified with a mineral acid to a pH of between about 1.5 and about 3.5.

24. A method according to claim 23 wherein said adding step comprises adding to the borate buffer solution a solution of bromonitromethane which is acidified with a mineral acid to a pH of between about 2.0 and about 3.0.

25. A method of inhibiting microbial growth in paper pulp, comprising adding to the paper pulp an acidified solution of bromonitromethane in an amount sufficient to inhibit the growth of microbes in the pulp.

26. A method according to claim 25 wherein said adding step comprises adding to the paper pulp a solution of bromonitromethane which is acidified with a mineral acid to a pH of less than about 4.0.

27. A method according to claim 26 wherein said adding step comprises adding to the paper pulp a solution of bromonitromethane which is acidified with a mineral acid to a pH of between about 1.5 and about 3.5.

28. A method according to claim 27 wherein said adding step comprises adding to the paper pulp a solution of bromonitromethane which is acidified with a mineral acid to a pH of between about 2.0 and about 3.0.

* * * * *

UNITED STATES PATENT AND TRADEMARK OFFICE
CERTIFICATE OF CORRECTION

PATENT NO  : 5,866,511
DATED      : February 2, 1999
INVENTOR(S): Dallmier et al.

It is certified that error appears in the above-identified patent and that said Letters Patent is hereby corrected as shown below:

In column 5, line 3, please change "NaHCO" to --$NaHCO_3$--.

Signed and Sealed this

Twentieth Day of March, 2001

Attest:

NICHOLAS P. GODICI

*Attesting Officer*   *Acting Director of the United States Patent and Trademark Office*